US009518303B2

(12) United States Patent
Pyles et al.

(10) Patent No.: US 9,518,303 B2
(45) Date of Patent: Dec. 13, 2016

(54) METHODS AND COMPOSITIONS FOR IDENTIFYING ENTEROVIRUS

(71) Applicants: THE BOARD OF REGENTS OF THE UNIVERSITY OF TEXAS SYSTEM, Austin, TX (US); Richard B. Pyles, Galveston, TX (US); Aaron L. Miller, Galveston, TX (US)

(72) Inventors: Richard B. Pyles, Galveston, TX (US); Aaron L. Miller, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/353,832

(22) PCT Filed: Oct. 25, 2012

(86) PCT No.: PCT/US2012/061960
§ 371 (c)(1),
(2) Date: Apr. 24, 2014

(87) PCT Pub. No.: WO2013/085631
PCT Pub. Date: Jun. 13, 2013

(65) Prior Publication Data
US 2015/0292041 A1    Oct. 15, 2015

Related U.S. Application Data

(60) Provisional application No. 61/551,389, filed on Oct. 25, 2011.

(51) Int. Cl.
*C12Q 1/68* (2006.01)
*C12Q 1/70* (2006.01)

(52) U.S. Cl.
CPC .................................... *C12Q 1/701* (2013.01)

(58) Field of Classification Search
None
See application file for complete search history.

(56) References Cited

U.S. PATENT DOCUMENTS 4,683,195 A    7/1987 Mullis
4,683,202 A    7/1987 Mullis
(Continued)

FOREIGN PATENT DOCUMENTS

WO        9014439        11/1990

OTHER PUBLICATIONS

Lee et al., "A Diverse Group of Previously Unrecognized Human Rhinoviruses are Common Causes of Respiratory Illnesses in Infants," PLoS One 3:2(10):e966 (2007).*
(Continued)

*Primary Examiner* — Janet L Andres
*Assistant Examiner* — M. Franco Salvoza
(74) *Attorney, Agent, or Firm* — Norton Rose Fulbright US LLP

(57) ABSTRACT

Certain embodiments of the invention include, but are not limited to PCR primer pairs, sequencing primers, and/or associated thermocycling protocols targeting a region identified by the inventors within the 5' untranslated region of enteroviruses for the purpose of identifying, subtyping, and/or classifying of virus in samples using nucleic acid sequencing. The sequencing procedures can use nucleic acid templates, such as cDNA or PCR amplicons, as a template for sequencing in medium to high throughput format that is cost effective and easily deployed to other clinical microbiology laboratories.

7 Claims, 3 Drawing Sheets

2-28-11 – 1.5% Agarose Gel
1. RV plasmid clone F9
2. RV plasmid clone B9
3. RV plasmid clone D5
4. RV plasmid clone A7
5. RV plasmid clone E8
6. NTC

(56) References Cited

U.S. PATENT DOCUMENTS

| | | | |
|---|---|---|---|
| 4,786,600 | A | 11/1988 | Kramer |
| 4,800,159 | A | 1/1989 | Mullis |
| 5,075,212 | A | 12/1991 | Rotbart |
| 5,422,252 | A | 6/1995 | Walker |
| 5,585,477 | A | 12/1996 | Kilpatrick |
| 5,691,134 | A | 11/1997 | Kilpatrick |
| 7,435,539 | B2 | 10/2008 | Oberste |
| 8,119,338 | B2 | 2/2012 | Lee |
| 2006/0035228 | A1 | 2/2006 | Soderlund |
| 2010/0143881 | A1 | 6/2010 | Lu |
| 2010/0233677 | A1 | 9/2010 | Liggett |

OTHER PUBLICATIONS

Revill et al., Viral Genotyping and the Sequencing Revolution, Lennette's Laboratory Diagnosis of Viral Infections, Fourth Edition, 40-58.
Longtin et al., 2010, Emerging Infectious Diseases, 16 (9): 1463-1465.
Li et al., 2005, J. Clin. Microbiol., 43 (8): 3835-3839.
Lim et al., 1960, J. Immunol., 84: 309-317.
Melnick et al., 1973, Bull. WHO, 48: 263-268.
Rotbart et al., 1988, Mol. Cell. Probes, 2: 65-73.
Rotbart, 1990, J Clin. Microbiol., 28: 438-442.
Chapman et al., 1990, J Clin. Microbiol., 28: 843-850.
Hyypia et al., 1989, J Gen. Virol., 70: 3261-3268.
Olive et al., 1990, J Gen. Virol., 71: 2141-2147.
Loeffelholz et al., 2011, Journal of Clinical Microbiology, 49(12): 4083-4088.
Yang et al., 1992, Virus Res., 24: 277-296.
Zoll et al., 1992, J Clin. Microbiol., 30: 160-165.
Muir et al., 1993, J Clin. Micro., 31: 31-38.
Drebot et al., 1994, J Med. Virol., 44: 340-347.
Rotbart et al., 1994, J Clin. Microbiol., 32: 2590-2592.
Diedrich et al., 1995, J Med. Viral., 46: 148-152.
Arola et al., 1996, J Clin. Microbiol., 34: 313-318.
Bailly et al., 1996, Virology, 215: 83-96.
Holland et al., 1998, J Clin. Microbiol., 36: 1588-1594.
Gen Bank accession No. DQ473509.
Infosheet FilmArray Respiratory Panel—BioFire Diagnostics.
International search report for PCT/US2012/061960.

* cited by examiner 2-28-11 – 1.5% Agarose Gel
1. RV plasmid clone F9
2. RV plasmid clone B9
3. RV plasmid clone D5
4. RV plasmid clone A7
5. RV plasmid clone E8
6. NTC Conventional Sanger sequencing vs. Pyrosequencing

```
Plasmid_clone_A7_Sanger      GCCGGAGGACTCAAAGTGAGCACACGC 27
Plasmid_clone_A7_Pyro        GCCGGAGGACTCAAAGTGAGCACACGC 27
                             ***************************

Plasmid_clone_D5_Sanger      GCCGGAGGACTCAAGGTGAGCACACGC 27
Plasmid_clone_D5_Pyro        GCCGGAGGACTCAAGGTGAGCACACGC 27
                             ***************************

Plasmid_clone_E8_Sanger      GCCGGAGGACTCACAATTAGCAAACGC 27
Plasmid_clone_E8_Pyro        GCCGGAGGACTCACAATTAGCAAACGC 27
                             ***************************

Plasmid_clone_F9_Sanger      GCCGGAGGACTCAAGGTGAGCACACGC 27
Plasmid_clone_F9_Pyro        GCCGGAGGACTCAAGGTGAGCACACGC 27
                             ***************************
```

FIG. 2 cDNA vs. Nested PCR template comparison

```
180E_NPS_E2V1_cDNA           GCCGGAGGACTCATTGGTAGCACACGG 27
180E_NPS_E2V1_Nested_PCR     GCCGGAGGACTCATTGGTAGCACACGG 27
                             ***************************

192E_E1V1_cDNA               GCCGGAGGACTCAAAGCGAGCACACGG 27
192E_E1V1_Nested_PCR         GCCGGAGGACTCAAAGCGAGCACACGG 27
                             ***************************

197E_E3V1_cDNA               GCCGGAGGAATCAAAACAAGCACACGG 27
197E_E3V1_Nested_PCR         GCCGGAGGAATCAAAACAAGCACACGG 27
                             ***************************

217E_NPS_E1V1_cDNA           GCCGGAGGACTCAAAGTGAGCACACGG 27
217E_NPS_E1V1_Nested_PCR     GCCGGAGGACTCAAAGTGAGCACACGG 27
                             ***************************
```

FIG. 3

METHODS AND COMPOSITIONS FOR IDENTIFYING ENTEROVIRUS

This application is a U.S. national stage filing of International Application No. PCT/US2012/061960 filed Oct. 25, 2012, which claims priority to U.S. Provisional Application Ser. No. 61/551,389 filed Oct. 25, 2011. This application claims priority to the above-referenced applications. Each application referenced above is incorporated herein by reference in its entirety.

This invention was made with government support under R01 DC005841 awarded by the National Institutes of Health. The government has certain rights in the invention.

A sequence listing required by 37 CFR 1.821-1.825 is being submitted electronically with this application. The sequence listing is incorporated herein by reference.

BACKGROUND ART

Enteroviruses are responsible for large numbers of infections. There may be between 30 million to 50 million illnesses that are ascribable to enteroviruses each year in the United States (Center for Disease Control and Prevention, MMWR 46:748-750, 1997-1999; Strikas et al., J. Infect. Dis. 146:346-351, 1986; Rotbart in Human Enterovirus Infections, H. A. Rotbart (ed.) ASM Press, Washington, D.C., pp. 401-418, 1995). Enterovirus infections lead to 30,000 to 50,000 hospitalizations each year for aseptic meningitis, myocarditis, encephalitis, acute hemorrhagic conjunctivitis, nonspecific febrile illnesses, and upper respiratory infections (Melnick, Biologicals 21:305-309, 1993; Morens et al., in Human Enterovirus Infections, H. A. Rotbart (ed.) ASM Press, Washington, D.C., pp. 3-23, 1995; Melnick in Fields Virology (B. N. Fields et al. (eds.)) 3rd ed., Lippincott-Raven Publishers, Philadelphia, pp. 655-712, 1996). Enteroviruses are also implicated in acute flaccid paralysis in animal models, as well as in dilated cardiomyopathy and have been linked to chronic fatigue syndrome (Clements et al., J. Med. Virol. 45:156-161, 1995).

One of the issues in both diagnostic and epidemiological studies of enterovirus (EV)(which includes the extremely common rhinovirus (RV)) infections in children and adults is that these viruses share an extremely high degree of sequence similarity. Quantitative PCR (qPCR) for RV and other EV viruses often results in cross-priming that can lead to misidentification of the virus present in clinical material and connection of disease states to the wrong species of virus. Further, it is almost impossible to successfully identify individuals that are suffering from co-infections of RV and another EV by standard qPCR methods.

Thus, there remains a need for compositions and methods for identifying, subtyping, and/or classifying viral infections like enterovirus infections in medium to high throughput, cost effective fashion.

DISCLOSURE OF INVENTION

Sequence information provides reliable data for microbial genotyping applications. However, standard methods used to assess discriminatory regions of microbial genes can be time-consuming, may require species-specific probes or gel electrophoresis, or are susceptible to the presence of unknown mutations that alter the outcomes of assays (e.g., primer hybridization). Tracking outbreaks or the emergence of genetically drifted species is of critical importance to fields of infection control and viral pathology.

Certain embodiments of the invention include, but are not limited to PCR primer pairs, sequencing primers, and/or associated thermocycling protocols targeting a region identified by the inventors within the 5' untranslated region (5'UTR) of enteroviruses (EV) for the purpose of identifying, subtyping, and/or classifying of virus in samples using nucleic acid sequencing. The sequencing procedures can use nucleic acid templates, such as cDNA or PCR amplicons, as a template for sequencing in medium to high throughput format that is cost effective and easily deployed to other clinical microbiology laboratories.

Certain embodiments are directed to an isolated enterovirus (EV) nucleic acid segment of 55, 56, 57, 58, 59, 60, 61, 62, 63, 64, 65, 66, 67, 68, 69, 70, 71, 72, 73, 74, 75, 80, 85, 90 nucleotides to 70, 71, 72, 73, 74, 75, 80, 85, 90, 95, 100, 125, 150, 200 nucleotides in length, including all values and ranges there between, of an enterovirus, such as a rhinovirus, 5' untranslated region (5'UTR). The nucleic acid segment can comprise a 5'UTR nucleic acid segment corresponding to a 5'UTR segment of human rhinovirus A defined as the nucleic acid segment having a nucleotide sequence corresponding to that of SEQ ID NO:5. In this instance, the term "correspond" or "corresponding sequence" refers to a nucleic acid segment that can be identified by sequence similarity and/or location with a viral genome. The corresponding sequences can be aligned or analyzed and the sequence difference(s) between two or more corresponding or analogous sequences can be determined. A corresponding or analogous sequence will have a sequence identity of 70, 75, 80, 85, 90, 95, or 100%. In certain aspects the corresponding sequences can have a consensus of YKGACATG-GTGTGAAGAGTCTATTGAGCTCMASTTGRKAGTC-CTCCGGCCCCTGA ATGCGGCTAATCC (SEQ ID NO:36), wherein Y designates a C or T(U), K designates a G or T(U), M designates an A or C, S designates a G or C, R designates an A or G. The isolated nucleic acid segment can be 70, 75, 80, 85, 90, 95, or 100% identical to the consensus sequence of SEQ ID NO:36. The nucleic acid segment can be a rhinovirus nucleic acid segment, such as a Human rhinovirus A, Human rhinovirus B, or Human rhinovirus C nucleic acid segment. In certain aspects the isolated nucleic acid segment can have a nucleotide sequence of a known or unknown rhinovirus, such as Human rhinovirus A serotypes HRV-1, HRV-2, HRV-7, HRV-8, HRV-9, HRV-10, HRV-11, HRV-12, HRV-13, HRV-15, HRV-16, HRV-18, HRV-19, HRV-20, HRV-21, HRV-22, HRV-23, HRV-24, HRV-25, HRV-28, HRV-29, HRV-30, HRV-31, HRV-32, HRV-33, HRV-34, HRV-36, HRV-38, HRV-39, HRV-40, HRV-41, HRV-43, HRV-44, HRV-45, HRV-46, HRV-47, HRV-49, HRV-50, HRV-51, HRV-53, HRV-54, HRV-55, HRV-56, HRV-57, HRV-58, HRV-59, HRV-60, HRV-61, HRV-62, HRV-63, HRV-64, HRV-65, HRV-66, HRV-67, HRV-68, HRV-71, HRV-73, HRV-74, HRV-75, HRV-76, HRV-77, HRV-78, HRV-80, HRV-81, HRV-82, HRV-85, HRV-88, HRV-89, HRV-90, HRV-94, HRV-95, HRV-96, HRV-98, and HRV-100; Human rhinovirus B serotypes HRV-3, HRV-4, HRV-5, HRV-6, HRV-14, HRV-17, HRV-26, HRV-27, HRV-35, HRV-37, HRV-42, HRV-48, HRV-52, HRV-69, HRV-70, HRV-72, HRV-79, HRV-83, HRV-84, HRV-86, HRV-91, HRV-92, HRV-93, HRV-97, and HRV-99; or a nucleotide sequence that differs by 1, 2, 3, 4, or more nucleotides from a known rhinovirus sequence. In a further aspect, the isolated nucleic acid segment is single or double stranded. In certain aspects the isolated nucleic acid segment comprises or consist of an enterovirus nucleic acid sequence corresponding to SEQ ID NO:4 or the complement of SEQ ID NO:4. The sequence listing implicitly discloses the complement of the polynucleotide provided. Thus, for example, SEQ ID NO:4 and SEQ ID NO:5 also represent the complement of the their sequence.

In certain aspects one or both strands of a nucleic acid segment can be coupled to the same or different affinity agents, which includes but is not limited to, biotin, fucose, dinitrophenyl (DNP), metal or metal cluster, and the like. As used herein, the term "affinity agent" refers to any of a variety of compounds that can be incorporated into or couple to a nucleic acid and which can selectively bind a "binding agent", thus allowing for immobilization of the nucleic acid bearing the affinity agent—biotin/streptavidin is an example of an affinity agent/binding agent pair. Binding agents can be coupled or attached to other supports or surfaces such as metal or polymeric supports or surfaces, or metal or polymeric beads or chips.

Certain embodiments are directed to an oligonucleotide or an oligonucleotide primer. Such primers can be used to isolate, amplify, and/or analyze a nucleic acid segment described herein. In certain aspects one, two, or more first oligonucleotide primers of 19, 20, 21, 22, 23, 24, 25, 26, 27, 28, 29, or 30 to 25, 26, 27, 28, 29, 30, 31, 32, 33, 34, 35, 36, 37, 38, 39, or 40 nucleotides, including all values and ranges there between, comprises a nucleotide sequence that is at least 70, 75, 80, 85, 90, 95 or 100% identical to SEQ ID NO:1. In certain aspects a combination of first primers will differ by 1, 2, 3, or 4 nucleotides, e.g., 3' or 5' terminal nucleotides. In a further aspect a second oligonucleotide primer of 18, 19, 20, 21, 22, 23, 24, 25, 26, 27, 28, 29, or 30 to 25, 26, 27, 28, 29, 30, 31, 32, 33, 34, 35, 36, 37, 38, 39, or 40 nucleotides, including all values and ranges there between, comprising a nucleotide sequence that is at least 70, 75, 80, 85, 90, 95 or 100% identical to SEQ ID NO:2. In still a further aspect the first oligonucleotide primer, second oligonucleotide primer, or first oligonucleotide primer and second oligonucleotide primer are coupled to an affinity agent. In certain aspects a first oligonucleotide primer consist of the nucleotide sequence of SEQ ID NO:1. In a further aspect a second oligonucleotide primer consist of the nucleotide sequence of SEQ ID NO:2.

Certain embodiments are directed to a kit comprising the first oligonucleotide primer and/or the second oligonucleotide primer as described herein. In certain aspects the kit further comprises an oligonucleotide of 15, 16, 17, 18, 19, 20, 21, 22, 23, 24, 25, 26, 27, 28, 29, or 30 to 25, 26, 27, 28, 29, 30, 31, 32, 33, 34, 35, 36, 37, 38, 39, or 40 nucleotides having a nucleotide sequence that is at least 70, 75, 80, 85, 90, 95 or 100% identical to SEQ ID NO:3.

Certain embodiments are directed to methods of identifying enterovirus, such as rhinovirus in a sample. The methods can comprise isolating a nucleic acid segment of an enterovirus or rhinovirus 5'UTR comprising a nucleic acid segment corresponding or analogous to a nucleic acid segment of rhinovirus A defined in SEQ ID NO:5, wherein the isolated nucleic acid has a length of 50, 55, 60, 65, 70, 75, 80, 90, 95, 100, 105, 110, 115, 120, 125 nucleotides to 100, 105, 110, 115, 120, 125, 150, 155, 160, 165, 170, 175, 200, up to 500 nucleotides, including all values and ranges there between. In certain aspects the methods include determining the nucleotide sequence of the isolated nucleic acid segment, wherein the nucleotide sequence identifies an enterovirus, such as a rhinovirus, in the sample. In certain aspects more than 1, 2, 3, 4, 5 or more enterovirus or rhinovirus are present in a sample. In a further aspect a plurality of isolated nucleic acid segments are isolated and/or sequenced. In still a further aspect the isolated nucleic acid is an amplicon, such as, but not limited to a PCR amplicon. In further aspects the nucleotide sequence is determined by pyrosequencing. The sample can be a biological fluid such as blood, urine, lymph, sputum, saliva; or a tissue sample.

As used herein the terms "specific to" or "specific for" a target sequence, in relation to a nucleic acid sequence such as an oligonucleotide sequence, relate to a nucleotide sequence that hybridizes or anneals, under conditions used in given circumstances (e.g., temperature, salt concentration, etc.), to the target but does not hybridize under those circumstances to sequences that are not target sequences providing specificity of hybridization or annealing. Nucleotide sequences that are specific for a particular target, such as an enterovirus and/or a rhinovirus target sequences, are contemplated. Oligonucleotides specific to or specific for an enterovirus and/or a rhinovirus are those that include bases that are complementary to the corresponding base on the target.

Further as used herein, "specificity" of a nucleic acid sequence for a target sequence also encompasses nucleic acids and oligonucleotides having a small number of nucleotides, which may not be complementary to the corresponding nucleotides of the target sequence. Such sequences are still "specific" for the target sequence, as used herein, as long as the extent of deviation from complementarity remains functionally of no consequence. In particular, such a sequence is "specific" for the target sequence as long as it hybridizes effectively to the target sequence but does not hybridize to any sequence that is not a target sequence, under the conditions used in given circumstances.

As used herein, an "amplicon" relates to a double stranded nucleic acid segment having a size and sequence that results from an amplification procedure, such as a PCR. The primer binding sites on the target nucleic acid governs amplicon size. The amplified segment of the target nucleic acid becomes the prevalent product of the amplification procedure after a number of cycles of amplification. The amplified segment can be isolated and analyzed by various methods known in the art, such as pyrosequencing.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The following drawings form part of the present specification and are included to further demonstrate certain aspects of the present invention. The invention may be better understood by reference to one or more of these drawings in combination with the detailed description of the specification embodiments presented herein.

FIG. 2. Validation of sequencing: conventional Sanger sequencing compared to pyrosequencing. plasmid clone A7=SEQ ID NO:25, plasmid clone D5=SEQ ID NO:37, plasmid clone E8=SEQ ID NO:12, plasmid clone F9=SEQ ID NO:37.

FIG. 3. Validation of sequencing: template cDNA compared to PCR amplicon template. 180E NPS E2V1=SEQ ID NO:38, 192E E1V1=SEQ ID NO:24, 197E E3V1=SEQ ID NO:14, 217E NPS E1V1=SEQ ID NO:22.

DESCRIPTION

Figure 1:
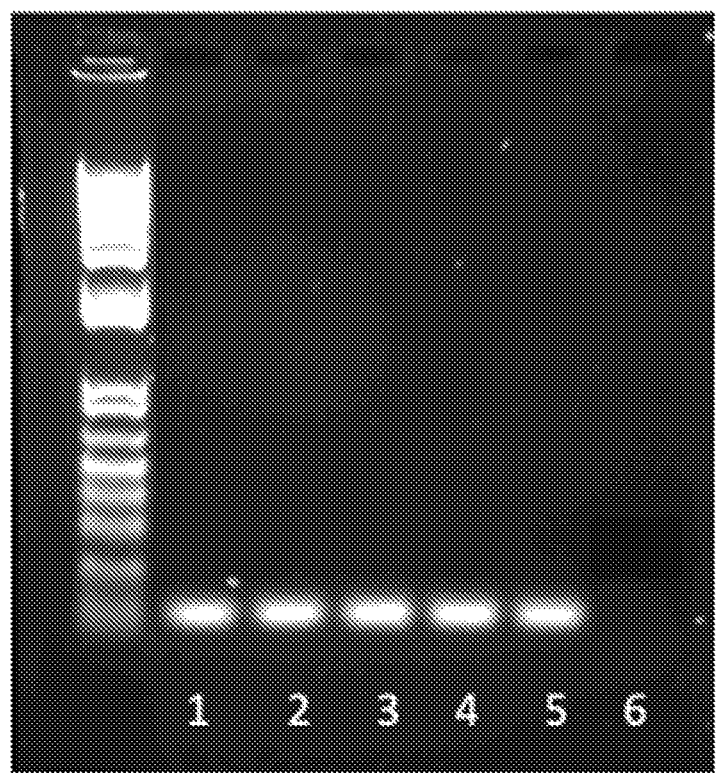
FIG. 1. Agarose gel analysis of PCR primers.

I. Enterovirus Genus of the Family Picornaviridae

The family Picornaviridae includes non-enveloped, positive-stranded RNA viruses with an icosahedral capsid. The name Picornaviridea is derived from pico, meaning small, and RNA, referring to the ribonucleic acid genome, so "picornavirus" literally means small RNA virus. Picornaviruses are classified as group IV viruses as they contain a single stranded, positive sense RNA genome of between 7.2 and 9.0 kb (kilobases) in length. Like most positive sense RNA genomes, the genetic material alone is infectious—although substantially less virulent than if contained within the viral particle. Unlike mammalian mRNA, picornaviruses do not have a 5' cap but a virally encoded protein known as VPg. And like mammalian mRNA, the picornavirus genome does have a poly(A) tail at the 3' end. Both ends of the picornavirus genome contain an untranslated region—a 5'UTR and a 3'UTR. The 5'UTR is longer, being around 600-1200 nucleotides (nt) in length, than the 3'UTR, which is around 50-100 nt. The rest of the genome encodes structural proteins at the 5' end and non-structural proteins at the 3' end in a single polyprotein.

Picornaviruses are separated into 12 distinct genera and include many important pathogens of humans and animals (Mettenleiter and Sobrino (editors), (2008), Animal Viruses: Molecular Biology, Caister Academic Press). The genera include Enterovirus (including rhinovirus), Cardiovirus, Aphthovirus, Hepatovirus, Parechovirus, Erbovirus, Kobuvirus, Teschovirus, Sapelovirus, Senecavirus, Tremovirus, and Avihepatovirus. Certain aspects of the invention are directed to typing or subtyping virus of the genus Enterovirus.

Enteroviruses are a large and diverse group of picornavirus with a genomic RNA of approximately 7,500 bases. An enterovirus genome typically comprises a 5'UTR followed by an open reading frame coding for a polyprotein precursor of MW 240-250×10$^3$ Da followed by a 3'UTR and a poly (A) tract. In the polyprotein, the sequence of gene products begins 1A, 1B, 1C, 1D, and 2A. 1A through 1D are the structural proteins VP4, VP2, VP3, and VP1 of the viral capsid, respectively; VP1 is followed in the open reading frame by a nonstructural protein 2A. Enteroviruses are known to have a high mutation rate due to low-fidelity replication and frequent recombination (Li et al. *J. Clin. Microbiol.* 43 (8): 3835-9, 2005). After infection of the host cell, the genome is translated in a cap-independent manner into the single polyprotein, which is subsequently processed by virus-encoded proteases into the structural capsid proteins and the nonstructural proteins, which are mainly involved in the replication of the virus (Merkle et al., *J. Virol.* 76 (19): 9900-909, 2002).

The enterovirus genus includes Bovine enterovirus, Human enterovirus A, Human enterovirus B, Human enterovirus C, Human enterovirus D, Human rhinovirus A, Human rhinovirus B, Human rhinovirus C, Porcine enterovirus B, and Simian enterovirus A.

Within these species there are numerous serotypes and subtypes that include Human enterovirus A serotypes CV-A2, CV-A3, CV-A4, CV-A5, CV-A6, CV-A7, CV-A8, CV-A10, CV-A12, CV-A14, and CV-A16; Human enterovirus B serotypes CV-B1, CV-B2, CV-B3, CV-B4, CV-B5, CV-B6, CV-A9, and CV-A23; Human enterovirus C serotypes CV-A1, CV-A11, CV-A13, CV-A17, CV-A19, CV-A20, CV-A21, CV-A22, and CV-A24; Human enterovirus B serotypes E-1, E-2, E-3, E-4, E-5, E-6, E-7, E-8, E-9, E-11, E-12, E-13, E-14, E-15, E-16, E-17, E-18, E-19, E20, E-21, E-24, E-25, E-26, E-27, E-29, E-30, E-31, E-32, and E-33; Human enterovirus A serotypes EV-71, EV-76, EV-89, EV-90, EV-91, and EV-92; Human enterovirus B serotypes EV-69, EV-73, EV-74, EV-75, EV-77, EV-78, EV-79, EV-80, EV-81, EV-82, EV-83, EV-84, EV-85, EV-86, EV-87, EV-88, EV-93, EV-97, EV-98, EV-100, EV-101, EV-106, and EV-107; Human enterovirus C serotypes EV-95, EV-96, EV-99, EV-102, EV-104, EV-105, and EV-109; Human enterovirus D serotypes EV-68, EV-70, and EV-94; Human rhinovirus A serotypes HRV-1, HRV-2, HRV-7, HRV-8, HRV-9, HRV-10, HRV-11, HRV-12, HRV-13, HRV-15, HRV-16, HRV-18, HRV-19, HRV-20, HRV-21, HRV-22, HRV-23, HRV-24, HRV-25, HRV-28, HRV-29, HRV-30, HRV-31, HRV-32, HRV-33, HRV-34, HRV-36, HRV-38, HRV-39, HRV-40, HRV-41, HRV-43, HRV-44, HRV-45, HRV-46, HRV-47, HRV-49, HRV-50, HRV-51, HRV-53, HRV-54, HRV-55, HRV-56, HRV-57, HRV-58, HRV-59, HRV-60, HRV-61, HRV-62, HRV-63, HRV-64, HRV-65, HRV-66, HRV-67, HRV-68, HRV-71, HRV-73, HRV-74, HRV-75, HRV-76, HRV-77, HRV-78, HRV-80, HRV-81, HRV-82, HRV-85, HRV-88, HRV-89, HRV-90, HRV-94, HRV-95, HRV-96, HRV-98, and HRV-100; Human rhinovirus B serotypes HRV-3, HRV-4, HRV-5, HRV-6, HRV-14, HRV-17, HRV-26, HRV-27, HRV-35, HRV-37, HRV-42, HRV-48, HRV-52, HRV-69, HRV-70, HRV-72, HRV-79, HRV-83, HRV-84, HRV-86, HRV-91, HRV-92, HRV-93, HRV-97, and HRV-99; Human enterovirus C serotypes PV-1, PV-2, and PV-3.

The various members of the human enteroviruses, including Human rhinoviruses (RV), cause a wide range of symptoms, syndromes, and diseases. Human RV are the most common viral agents in humans, having over 110 serologic types responsible for about 30-50% of all the cases of common colds and associated upper respiratory tract complications in both adults and children. Other diseases or conditions caused by enterovirus include acute benign pericarditis, acute flaccid paralysis, acute hemorrhagic conjunctivitis, aseptic meningitis, various exanthemas, carditis, croup, encephalitis, enanthema, gastrointestinal disease, hepatitis, hand-foot-and-mouth disease, various respiratory diseases, myocarditis, neonatal disease including multi-organ failure, pericarditis, pleurodynia, rash, and undifferentiated fever. In general, the syndromes are not correlated with particular enterovirus serotypes, nor does a serotype specifically correlate with a particular disease, although in certain cases serotypes do correlate with particular diseases.

It is important to identify the serotype or subtype of an enterovirus infection in a subject (e.g., a patient). Knowledge of the serotype can provide useful guidance to a physician in determining a course of treatment for a disease. For example, the appropriately identified immune globulin having a sufficient titer may be administered to immune-compromised patients. Furthermore, an antiviral drug such as Pleconaril (Viropharma) may differ in its relative efficacy against different serotypes or subtypes. Additionally, an understanding of the geographic and chronological development of an enterovirus infection in a population can influence preventive measures among the members of the population to minimize the spread of the disease. Furthermore, it is useful from a broader perspective to track the incidence and distribution of an enterovirus disease from an epidemiological point of view.

Various serotypes can be propagated in different cell culture hosts, and in different animal model hosts. In the animal hosts, different symptomology has also provided typing information. These classical assays provide ways of distinguishing the serotypes but are not definitive and can lead to misidentifications. Nevertheless, some enterovirus serotypes do not replicate in cell culture. It has been observed that the virus(es) in 25% to 35% of patient specimens is(are) not identified by cell culture for a variety of reasons (Rotbart in Human Enterovirus Infections, H. A. Rotbart (ed.) ASM Press, Washington, D.C., pp. 401-418, 1995). Furthermore, such culturing and classification procedures are costly, time-consuming, subject to experimental variation, and not amenable to repetitive or extensive application in the field.

The serotypes of non-polio enteroviruses have been identified during the past several decades using classical immunological neutralization assays based on a panel of specific antibodies. Application of such a determination to a clinical sample is generally impractical and inconvenient because it is expensive and has a research use only application. Although a number of neutralization sites have been localized to the VP1 protein of enterovirus particles, the exact identity of the epitopes responsible for serotype specificity remain unknown. Serotyping has generally been carried out using intersecting pools of antisera, the Lim and Benyesh-Melnick (LBM) pools, which were originally defined in 1960 (Lim et al., J. Immunol. 84:309-317, 1960). The antiserum pools currently distributed by the World Health Organization cover 42 serotypes in 8 pools (Melnick et al., Bull. WHO 48:263-268, 1973). Analysis of the neutralization pattern affords an identification of serotype. Clearly, this is a cumbersome and painstaking process. Additionally, the supply of the antisera is limited or difficult to maintain creating serious quality assurance issues. Problems in sero-typing more recent isolates have been ascribed to pronounced intratypic antigenic variation (Melnick, Enteroviruses: polioviruses, coxsackie viruses, echoviruses, and newer enteroviruses. In Fields Virology (Fields et al., (Eds.) 3rd Ed., Lippincott-Raven Publishers, Philadelphia, pp. 655-712, 1996; Melnick et al., Bull. WHO 63:453-550, 1985; Wigand et al., Arch. Ges. Virusforsch. 12:29-41, 1962; Wenner et al., Am J. Epidemiol. 85:240-249, 1967; Duncan, Arch. Ges. Virusforsch. 25:93-104, 1968). This has been explained by pointing out that enteroviruses, being RNA viruses, undergo spontaneous mutation at a very high rate, which can lead to genetic drift, with the potential of producing antigenic variants such that a neutralization assay would produce a false negative result.

More recently assays based on nucleic acid detection have been developed. Probe hybridization assays directed either to RNA or to cDNA have been used to detect non-polio enteroviruses (Rotbart et al., Mol. Cell. Probes 2:65-73, 1988; Rotbart, J. Clin. Microbiol. 28:438-442, 1990; Chapman et al., J. Clin. Microbiol. 28: 843-850, 1990; Hyypia et al., J. Gen. Virol. 70:3261-3268, 1989; Olive et al., J. Gen. Virol. 71:2141-2147, 1990; Gilmaker et al., J. Med. Virol. 38:54-61, 1992; Yang et al., Virus Res. 24:277-296, 1992; Zoll et al., J. Clin. Microbiol. 30:160-165, 1992; Muir et al., J. Clin. Micro. 31:31-38, 1993; Drebot et al., J. Med. Virol. 44:340-347, 1994; Rotbart et al., J. Clin. Microbiol. 32:2590-2592, 1994). In the absence of nucleic acid sequence information for the non-polio enteroviruses, most of these probes have targeted the highly conserved 5' non-coding region of the viral genomes. Additionally, RNA probes directed to the VP1 capsid gene have been used on a limited basis to identify some of the CBs and a few closely related CAs (Cova et al., J. Med. Virol. 24:11-18, 1988; Alksnis et al., Mol. Cell. Probes 3:103-108, 1989; Petitjean et al., J. Clin. Microbiol. 28:307-311, 1990). More recently, oligonucleotides having sequences based on the VP4-VP2 junction have been applied as diagnostic and epidemiologic tools (Drebot et al., J. Med. Virol. 44:340-347, 1994; Arola et al., J. Clin. Microbiol. 34:313-318, 1996; Kim et al., Arch. Virol. 142:853-860, 1997; Oberste et al., Virus Res. 58:35-43, 1998).

Reverse transcription (RT) coupled with the polymerase chain reaction (PCR) (RT-PCR) has been developed using enterovirus universal primers or broadly selective primers. Such primers are intended to amplify nucleotide regions from a large number of enterovirus serotypes in one diagnosis. One set of primers (Rotbart, J. Clin. Microbiol. 28:438-442, 1990) has been reported to amplify 60 of the 66 serotypes tested. A comparison of sequence identities of the various sets of universal primers with serotype sequences is given in Rotbart in Human Enterovirus Infections, H. A. Rotbart (ed.) ASM Press, Washington, D.C., pp. 401-418, 1995. Many of the universal primer sets are designed to amplify regions of the 5' untranslated region of the genome (see, for example, Drebot et al., J. Med. Virol. 44:340-347, 1994; Diedrich et al., J. Med. Virol. 46:148-152 (1995); Arola et al., J. Clin. Microbiol. 34:313-318, 1996; Bailly et al., Virology 215:83-96 (1996); and U.S. Pat. No. 5,075, 212).

International application WO 98/14611 discloses degenerate primers directed to the VP1 gene, which, when used in certain defined pairs, provide PCR amplification of enterovirus nucleic acids. Use of the specific primer pairs permits ascertaining whether a sample belongs to an enterovirus serotype, or to a small group of cognate serotypes, based on correlation of the pattern of the presence or absence of an amplicon with priming by the various primer pairs. This method does not rely on obtaining nucleotide sequences for accomplishing serotyping.

According to Holland et al. (*J. Clin. Microbiol.* 36:1588-1594, 1998) neither cell culture growth, nor PCR can successfully type enterovirus infections. They report an alternative typing protocol based on polyacrylamide gel electrophoretic fingerprinting of whole virus radiolabeled proteins. However, the database of viral protein profiles contains data for less than one-third of the known EV serotypes.

In the case of poliovirus, U.S. Pat. Nos. 5,585,477 and 5,691,134 disclose methods and oligonucleotide primers that are specific and sensitive for detecting all genotypes of poliovirus, as well as primers that are specific and sensitive for distinguishing the three serotypes of poliovirus, and methods for detecting poliovirus and/or distinguishing among the serotypes based on the use of the disclosed primers. Additionally PCT publication WO/1998/14611 discloses an extensive set of degenerate oligonucleotide primers for use in detecting the presence or absence of a non-polio enterovirus in a sample and to identify non-polio enterovirus serotypes. The primers are combined in pairs that detect various groupings of serotypes, and several amplification procedures are carried out in order to detect the presence of or absence of an amplicon in each case. A pooled grid of the results provides information useful in typing a non-polio enterovirus in a sample.

Thus, immunological methods for serotyping enterovirus infections are cumbersome and time consuming. They rely on an antigen-antibody reaction between antiserum pools established more than two decades ago, and whose supply may become limited. Antigen drift among RNA viruses, such as the enteroviruses, leads to a high probability that escape mutants will arise, and thereby escape not only serotyping, but perhaps detection as well. A second classical approach, cell culture coupled with whole animal host propagation and use of antisera for typing, is extremely cumbersome, expensive, and labor-intensive. Modern molecular biological methods similarly have important deficiencies as currently implemented. Probe assays generally tend to lack sensitivity. Furthermore, a probe directed to a conserved region, such as the 5' non-coding region of the non-polio enteroviruses, lacks specificity, and cannot be readily applied in typing a viral infection. RT-PCR has been implemented as a generic enterovirus diagnostic assay. In general, these assays fail to implement serotype-specific detection, so that typing is not currently available using RT-PCR. Holland et al. (*J. Clin. Microbiol.* 36:1588-1594, 1998) state that all typing methods in use or then currently under development are limited by virtue of the large number of different enterovirus serotypes, and as a consequence, the need for virus-specific reagents that would discriminate among them.

There remains a need for a simple and accurate typing procedure. Thus, there remains a need for an operationally elegant and efficient typing procedure that utilizes the specificity that resides, for example, in a target portion of the 5'UTR region. The present invention recognizes these needs, and addresses them.

II. Enterovirus Identification

Certain embodiments are directed to methods and compositions for amplifying and analyzing a target portion of the 5'UTR of enterovirus. In certain aspects the target portion of enterovirus comprises the nucleic acid sequence corresponding to CCCGTGTGCTCATCTTGAGTCCTCCGGC (SEQ ID NO: 5) of Human rhinovirus A, GenBank accession number DQ473509 (gi|95102533), which is incorporated herein by reference in its entirety as of the priority date of this and related applications. Oligonucleotide primers (amplification primers or amplimers) can be used to amplify a target region from nucleic acids in a sample. The forward or reverse amplification primer can be modified to assist in isolation and/or sequencing of the target region. In certain instances the forward or reverse amplification primers are coupled to an affinity agent, such as biotin. In certain aspects the forward primer, or a combination of two or more primers, can be 19 to 50 nucleotides in length and comprise the enterovirus sequence of SEQ ID NO:1 and/or a sequence that varies from SEQ ID NO:1 by 1, 2, 3 or 4 nucleotides. In certain aspects the variant nucleotide is the last 1, 2, 3, or 4, 3' nucleotides. If two or more primers are used the primers can be present in equimolar (1:1) concentration or as various molar ratios such as 1:0.9, 1:0.8, 1:0.7, 1:0.6, 1:0.5, 1:0.4, 1:0.3, 1:0.2, or 1:0.1, including all ratios there between. In a further aspect the nucleotide sequence of SEQ ID NO:1 is the only 5'UTR enterovirus sequence present in the forward amplification primer. In certain aspects the reverse amplification primer can be 18 to 50 nucleotides in length and comprise the enterovirus sequence of SEQ ID NO:2. In a further aspect the nucleotide sequence of SEQ ID NO:2 is the only 5'UTR enterovirus sequence present in the reverse amplification primer. A third primer can be used as a sequencing primer to sequence the amplified target region. In a further aspect the sequencing primer is a nested primer comprising a portion of the reverse or forward primer sequence. In certain aspects the sequencing primer has the nucleic acid of SEQ ID NO:3.

In one example, two PCR primers, one sequencing primer and associated thermocycling protocol for amplifying the enterovirus target region within the 5' untranslated domain of enteroviruses (EV) were designed for the purpose of identifying, subtyping and/or classifying enterovirus in a sample(s) using the nucleotide sequence of a portion of the 5'UTR. A pyrosequencing platform and associated chemistry were adapted to sequence isolated portions of enterovirus 5'UTR. A pyrosequencing assay was designed to use isolated nucleic acids, such as cDNA or EV amplification product (amplicon) from a validated quantitative PCR (qPCR), as a template for pyrosequencing PCR. In certain instances, the ability to use an amplicon for EV positive samples preserves irreplaceable stocks of clinical material-derived cDNA and provides for selecting only positive samples for downstream pyrosequencing analysis thus reducing costs and increasing productivity.

The forward and reverse amplification primers were designed after selection of an optimal sequence target region. The primers were synthesized in conjunction with desalting purification of non-modified primers and HPLC purification of any modified or biotinylated primers. Pyrosequencing PCR was carried out using PCR reagents and in conjunction with a thermocycler. Validation of the PCR assay was performed using plasmid clones derived from clinical material positive for RV that had been sequenced confirmed using conventional Sanger-based dideoxynucleotide sequencing methodology. These plasmids also provided control targets to produce synthetic mixes of material representing co-infection scenarios in advance of utilizing clinical material. Additional validation of the pyrosequencing assay was performed by comparing qPCR-derived templates obtained from clinical specimens and cDNA templates.

Figure 4:
FIG. 4. Dendrogram of 29 representatives RV and EV sequences from Galveston county of Table 1.

To illustrate the potential for molecular epidemiological assessments, a multiple sequence alignment and associated dendrogram were generated using 29 representative sequences (Table 1) depicting the discriminatory power of the methods to subtype RV and EV samples (FIG. 4).

TABLE 1

Multiple sequence alignment of 29 representative RV and EV sequences.

| Smp | Sequence | Size |
|---|---|---|
| 7 | GCCGGAGGAC-TCACT-GGTAGCA-CACGC (SEQ ID NO: 7) | 27 |
| 8 | GCCGGAGGAC-TCATT-GGTAGCA-CACGG (SEQ ID NO: 8) | 27 |
| 9 | GCCGGAGGAAATCACA-ATTAGCA-CACGG (SEQ ID NO: 9) | 28 |
| 10 | GCCGGAGGAA-TCACA-ATTAGCA-CACGG (SEQ ID NO: 10) | 27 |
| 11 | GCCGGAGGAATCAACA-ATTAGCA-CACGG (SEQ ID NO: 11) | 28 |
| 12 | GCCGGAGGAC-TCACA-ATTAGCA-AACGC (SEQ ID NO: 12) | 27 |
| 13 | GCCGGAGGAC-TCAAA-ACAAGCA-CACGG (SEQ ID NO: 13) | 27 |
| 14 | GCCGGAGGAA-TCAAA-ACAAGCA-CACGG (SEQ ID NO: 14) | 27 |
| 15 | GCCGGAGGAC-TCAAA-GCAAGCA-CACGG (SEQ ID NO: 15) | 27 |
| 16 | GCCGGAGGAC-TCACA-CATAGCA-CACGG (SEQ ID NO: 16) | 27 |
| 17 | GCCGGAGGAA-TCAAG-ATGAGCA-CACGG (SEQ ID NO: 17) | 27 |
| 18 | GCCGGAGGAG-TCAAG-ATGAGCA-CACGG (SEQ ID NO: 18) | 27 |
| 19 | GCCGGAGGAC-TCAAG-ATGAGCA-CACGG (SEQ ID NO: 19) | 27 |
| 5 | GCCGGAGGAC-TCAAT-GTGAGCA-CACGG (SEQ ID NO: 20) | 27 |
| 6 | GCCGGAGGAC-TCAAG-GTGAGCA-CACGG (SEQ ID NO: 21) | 27 |
| 1 | GCCGGAGGAC-TCAAA-GTGAGCA-CACGG (SEQ ID NO: 22) | 27 |
| 2 | GCCGGAGGACATCAAA-GTGAGCAGCACGG (SEQ ID NO: 23) | 29 |
| 3 | GCCGGAGGAC-TCAAA-GCGAGCA-CACGG (SEQ ID NO: 24) | 27 |
| 4 | GCCGGAGGAC-TCAAA-GTGAGCA-CACGC (SEQ ID NO: 25) | 27 |
| 20 | GCCGGAGGAC-TCAAA-ATGAGCA-CACTG (SEQ ID NO: 26) | 27 |
| 21 | GCCGGAGGAC-TCAAA-GTGAGCA-CAATA (SEQ ID NO: 27) | 27 |
| 22 | GCCGGAGGAC-TCAAAAGTGAGCA-CAATA (SEQ ID NO: 28) | 28 |
| 23 | GCCGGAGGAA-TCAAG-GTGAGCA-CAATA (SEQ ID NO: 29) | 27 |
| 24 | GCCGGAGGAC-TCAAG-GTGAGCA-CAGTA (SEQ ID NO: 30) | 27 |
| 25 | GCCGGAGGAC-TCAAA-GTGAGCA-CAGTA (SEQ ID NO: 31) | 27 |
| 26 | GCCGGAGGAC-TACCA-ATTAGCT-CAATA (SEQ ID NO: 32) | 27 |
| 27 | GCCGGAGGAC-TCCAA-GTGAGCG-CAGTA (SEQ ID NO: 33) | 27 |
| 28 | GCCGGAGGAC-TCAAA-GTGAGCA-CACTA (SEQ ID NO: 34) | 27 |
| 29 | GCCGGAGGAC-TCACATG-AAGCA-CACTC (SEQ ID NO: 35) | 27 |

A. Amplification

In certain aspects of the invention an enterovirus target region is prepared by amplification. Amplification of "fragments thereof" refers to production of an amplified nucleic acid containing less than a complete target nucleic acid (e.g., an enterovirus genome or cDNA thereof) or its complement. Such fragments may be produced by amplifying a portion of the target nucleic acid (e.g., a portion of the 5'UTR), for example, by using amplification primers that hybridize to, and initiate polymerization from, an internal position of the nucleic acid. Known amplification methods include, for example, transcription-mediated amplification, replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as QB-replicase (e.g., U.S. Pat. No. 4,786,600; PCT WO 90/14439, each of which is incorporated herein by reference). PCR amplification is well known and uses a DNA polymerase, primers and thermal cycling to synthesize multiple copies of the two complementary strands of DNA (e.g., U.S. Pat. Nos. 4,683,195, 4,683,202, and 4,800,159, each of which is incorporated herein by reference). LCR amplification uses at least four separate oligonucleotides to amplify a target and its complementary strand by using multiple cycles of hybridization, ligation, and denaturation (see EP Patent Application 0 320 308, which is incorporated herein by reference). SDA is a method in which a primer contains a recognition site for a restriction endonuclease such that the endonuclease will nick one strand of a hemi-modified DNA duplex that includes the target sequence, followed by amplification in a series of primer extension and strand displacement steps (see U.S. Pat. No. 5,422,252, which is incorporated herein by reference). It will be apparent to one skilled in the art that the amplification oligonucleotides disclosed herein are readily applicable to other amplification methods that use primer extension.

In certain aspects polymerase chain reaction (PCR) is used to amplify an enterovirus target region. As used herein, the term "PCR" is well known. Generally, PCR includes the steps of: (a) obtaining target nucleic acid molecules from a sample; (b) adding an aqueous solution including an enzyme, a buffer, dNTPs, and oligonucleotide primers to the sample; (c) amplifying the target DNA molecules by thermal cycling using two or more cycling steps (denaturation, annealing, and/or extension cycles) of the resultant mixture; and (d) detecting amplified nucleic acids, typically DNAs. The PCR may be performed in a polypropylene tube, a multi-well plate, an emulsion bubble, a fluidics chamber or a silicon-based micro PCR chip.

The present invention also provides an enterovirus/rhinovirus assay kit including amplification primers for subtyping enterovirus/rhinovirus. A kit may include the primers, a PCR solution, a buffer, an enzyme, and the like.

B. Sequencing

Once an amplicon of the target region is obtained, the sequence of the amplicon can be determined. A variety of methods are known in the art for determining the sequence of a nucleic acid that include, but are not limited to, pyrosequencing, chain termination sequencing, adaptor ligation sequencing (massively parallel signature sequencing (MPSS)), and reversible dye-terminator sequencing (Illumina Sequencing).

In certain aspects an amplicon is sequenced using pyrosequencing. Pyrosequencing can provide increased speed and identification of exact sequence variation. Pyrosequencing is a sequencing technology based on the iterative incorporation of specific nucleotides during primer-directed polymerase extension, providing real time sequence information. Pyrosequencing can also reduce costs of each assay.

In one embodiment, primers to a 5'UTR target region are designed using Pyromark™ Assay Design 2.0 software, e.g., forward amplification primer (SEQ ID NO:1), reverse amplification primer (SEQ ID NO:2), and sequencing primer (SEQ ID NO:3). An example of a rhinovirus genomic sequence is provided as SEQ ID NO:6. The designed primers are synthesized by Sigma-Genosys, or similar company providing synthesis services, with desalting purification used for the reverse amplification primer and the sequencing primer and HPLC purification used for biotinylated forward amplification primer.

Pyrosequencing PCR was carried out on a Qiagen Pyromark™ ID 96 pyrosequencing platform (Qiagen) using a final sequencing primer concentration of 0.3 µM and cyclic dispensation of 20 (GCAT). The master mix (per sample) includes 12.5 µl Bio-Rad Supermix (2×); 1.0 µl Forward primer (5 µM); 1.0 µl Reverse primer (5 µM); and water to volume. The template is amplified in 25 µl total reaction volume using PCR protocol defined as 95 C for 1:30; 95 C 0:15, 60 C 1:00, ×50; 72 C 5:00; and 4 C indefinite hold. The pyrosequencing PCR can use Bio-Rad iQSupermix PCR in conjunction with a C1000 thermocycler but other combinations could be used as well.

Initial validation of the PCR assay was performed using plasmid clones derived from clinical material positive for RV or EV that had been sequenced confirmed using conventional Sanger-based dideoxynucleotide sequencing methodology (FIG. 1). The plasmids also provided control targets to produce synthetic mixes of material representing co-infection scenarios in advance of utilizing clinical material.

Preparation of the PCR amplicons for pyrosequencing was performed using a Qiagen Pyromark Q96 vacuum workstation. Pyrosequencing was run in SQA mode on the Pyromark ID using Pyromark Gold reagents. Optimal conditions for the sequencing were empirically established and included an empirically derived cyclic dispensation order of 20 (GCAT) and a final sequencing primer concentration of 0.3 µM. The results of these studies are presented in FIG. 2 and indicate conventional Sanger and pyrosequencing methods are 100% concordant, validating the methodology. Further validation of the pyrosequencing assay was performed by comparing cDNA and qPCR-derived templates obtained from clinical specimens (FIG. 3). These studies indicated that for RV, cDNA and qPCR amplicon PCR templates yielded identical pyrosequencing results.

Specificity of the pyrosequencing assay was determined by analyzing samples previously identified as positive by qPCR for human coronaviruses 229E and OC43, influenza A, parainfluenza, metapneumovirus, respiratory syncytial virus, adenovirus and bocavirus. Such samples represent the most common upper respiratory infections in this patient population that would potentially confound the sequencing assay if it were not specific for RV/EV targets. Thirty-two qPCR negative samples were also evaluated. In every case, these validation tests did not result in viral sequence from any of the tested respiratory pathogens indicating that the assay is specific for RV/EV only. Surprisingly, 13 of the selected 32 qPCR negative samples yielded RV sequence demonstrating increased sensitivity of the pyrosequencing assay over the standard RV qPCR.

In an additional validation study of cDNAs from 101 RV positive clinical samples as identified by qPCR assay the inventors completed speciation studies using the optimized pyrosequencing system. Of the 101 positive samples, 97 yielded sequence consistent with RV Glade level subtypes while 4 samples failed to provide interpretable sequence results (likely due to decreased titer in the original sample). In parallel, cDNA from 30 qPCR positive EV samples (using the methods of Oberste et al., *Journal of Clinical Virology*, 49:73-73, 2010) were evaluated by the pyrosequencing system. Of these 30 samples, 25 also tested positive for RV by qPCR emphasizing the lack of fidelity with the qPCR alone approach. Pyrosequencing determined 21 of the samples to be RV while only 4 were mixed infections of EV and RV. Pyrosequencing of the final 5 samples exclusively positive for EV by qPCR, yielded 1 positive for human enterovirus, 2 mixed infections, 1 positive for RV, and 1 negative. Collectively, these results illustrate the utility and enhanced diagnostic and molecular epidemiological value for the pyrosequencing assay that clearly discriminated between cross-reactivity of RV and EV qPCR. To illustrate the potential for molecular epidemiological assessments, a multiple sequence alignment and associated dendrogram were generated using 29 representative sequences depicting the discriminatory power of our pyrosequencing assay to subtype RV and EV samples (Table 1 and FIG. 4).

The invention claimed is:

1. A method of amplifying enterovirus in a sample comprising:
   (a) amplifying a nucleic acid segment from the sample, wherein the nucleic acid segment is an enterovirus 5'UTR corresponding to a nucleic acid segment of rhinovirus A consisting of the nucleic acid sequence of SEQ ID NO:5 to produce an amplicon; and
   (b) sequencing the amplicon.

2. The method of claim 1, wherein more than one enterovirus is present in the sample.

3. The method of claim 2, wherein a plurality of amplicons are sequenced.

4. The method of claim 1, wherein the sequencing is by pyrosequencing.

5. The method of claim 1, wherein the sample is a blood, urine, lymph, sputum, saliva, or tissue sample.

6. The method of claim 1, wherein the amplifying step uses amplification primers comprising a nucleotide sequence of SEQ ID NO:1 and SEQ ID NO:2.

7. The method of claim 1, wherein the sequencing step uses a sequencing primer comprising a nucleic acid sequence of SEQ ID NO:3.

* * * * *

UNITED STATES PATENT AND TRADEMARK OFFICE
CERTIFICATE OF CORRECTION

PATENT NO. : 9,518,303 B2  Page 1 of 1
APPLICATION NO. : 14/353832
DATED : December 13, 2016
INVENTOR(S) : Pyles et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this
Twenty-fifth Day of September, 2018

Andrei Iancu
*Director of the United States Patent and Trademark Office*

SEQUENCE LISTING

<160> NUMBER OF SEQ ID NOS: 38

<210> SEQ ID NO 1
<211> LENGTH: 19
<212> TYPE: DNA
<213> ORGANISM: Artificial Sequence
<220> FEATURE:
<223> OTHER INFORMATION: synthetic oligo

<400> SEQUENCE: 1
tggacaaggt gcgaagagc                                                    19

<210> SEQ ID NO 2
<211> LENGTH: 18
<212> TYPE: DNA
<213> ORGANISM: Artificial Sequence
<220> FEATURE:
<223> OTHER INFORMATION: synthetic oligo

<400> SEQUENCE: 2
ggttagccgc attcaggg                                                     18

<210> SEQ ID NO 3
<211> LENGTH: 15
<212> TYPE: DNA
<213> ORGANISM: Artificial Sequence
<220> FEATURE:
<223> OTHER INFORMATION: synthetic oligo

<400> SEQUENCE: 3
tagccgcatt caggg                                                        15

<210> SEQ ID NO 4
<211> LENGTH: 65
<212> TYPE: DNA
<213> ORGANISM: Enterovirus

<400> SEQUENCE: 4
tggacaaggt gcgaagagcc ccgtgtgctc atcttgagtc ctccggcccc tgaatgcggc       60
taacc                                                                   65

<210> SEQ ID NO 5
<211> LENGTH: 28
<212> TYPE: DNA
<213> ORGANISM: Enterovirus

<400> SEQUENCE: 5
cccgtgtgct catcttgagt cctccggc                                          28

<210> SEQ ID NO 6
<211> LENGTH: 7129
<212> TYPE: DNA
<213> ORGANISM: Rhinovirus

<400> SEQUENCE: 6
ttaaaactgg gagtgagttg tccccactca ctctacccac gcggtgttgt acactgttat       60
tacggtaact ttgtatgcca gtttttgttc cctatcccc ctttaaagta acttagaagc       120
atgaacttac agaccaaaag gtgatgatca cccagatcat taaaggtcaa gcacttctgt      180
ttccccggtc aatgttgata tgcttcaaca aggcaaaaac aacagcgatc gttatccgca      240
agatgcctac acaaagctta gtacctcctt tgatggtatt tgtctggtcg ctcaggtgtt      300
tccccaacac tagacctggc agatgaggct agaaactccc cactggcgac agtgttctag      360

```
cctgcgtggc tgcctgcaca ccctttcggg tgtgaagcca aatactggac aaggtgcgaa      420 gagcccgtg tgctcatctt gagtcctccg gcccctgaat gcggctaacc ttaaacccgc       480
agccattact cacaatccag tgagcagatg gtcgtaatga gcaattgtgg gatgggaccg      540
actactttgg gtgtccgtgt ttcatgtttt actttatgac ttgcttatgg tgacaatata      600
tagagatata tattggcatc atgggcgctc aagtatctag acagaatgtt ggtacacatt      660
caactcaaaa catggtttca aatggatcta gtttgaatta tttcaacatt aattacttta      720
aggatgctgc ttctagtgga gcatctaaat tggaattttc acaagatccc agtaaattta     780
cagacccagt caaggatgtt ttagaaaagg gaatcccaac tttgcagtcg ccaacagttg      840
aagcctgtgg atactcggat agaattattc aaataacaag aggagattcc acaattacat      900
cacaggatgt agcaaatgct gttgtggggt acgggatatg ccacactac ttatcccctg       960 aagatgctac agctatagat aaaccaacac gccctgatac gtcatctaat aggttctaca     1020
ctttagaaag taaaatttgg acaagagact cgaaaggttg gtggtggaaa ttgccagatg     1080
cactcaagga aatgggagtt tttggacaga acatgtatta ccatttccta gggagaagtg     1140
gctatacaat ccatgtacaa tgtaatgcta gcaaattcca ccagggcaca ttgatagtgg     1200
ctgctatacc agaacatcaa ttggcaagtg cagagaaagg aaatgttaat actggctata     1260
attacacaca ccctggtgaa aggggtaggg atgttgggca ggagagagaa agtaccagct     1320
atcagcccag tgatgataat tggcttaatt ttgatggcac tctattgggt aatataacca     1380
ttttcccaca tcaatttata aacttgagaa gcaacaattc tgcaacactt attctcccat     1440
atgtaaatgc tgtacctatg gactctatgc ttagacacaa taattggagt ttggtaataa     1500
tcccaatttg tcctctagaa actaatggtg gtgatgtcac tgtacctata acaatatcta     1560
ttagtccaat gtttgctgaa ttctctggag cgcgagcccg tagccaggga ttgccagtat     1620
taatgacccc aggatctggt cagttcatga caactgatga ttaccagtcg cccagtgcat     1680
taccatggtt ccattcaaca aaggaaatat ttatcccagg tcaagtacat aatttggcag     1740
aactgtgtca ggttgataca attataccaa ttaattatac aacagcaaat acaactagtg     1800
ttaatatgta cactgtggtg ctgcaaaaag aaaaccctgg aacagaagtt tttgctatga     1860
gagttgacat agcaacacaa cctctagcta caacattaat tggagagatt gccagttatt     1920
atacacattg gactggtagt ttgagattta gcctcatgtt ttgcggaacg gcaggcacca     1980
cacttaaatt actagttgcc tacacacctc ctggaattgc caagccagaa acaggaaag     2040 acgcaatgct tggtacccat gttgtttggg atgttggcct acaatcaacc atatcaatga     2100
ttgtgccttg ggtcagtgct agtcattta gaaacaccac accagataaa ttctcacaag      2160
caggatacat aacatgttgg taccaaacca ctcttgtcac acccctagc acgcctgcca       2220 cagccagaat gctctgtttt gtatcagggt gtaaggattt ctgcctacgc atggctagag     2280
acactaactt acataaacaa gttggaccca tcacacaaaa tccagttgaa aaatatgttg     2340
acagtgttct gaatgaggtg ttagttgttc ccaatattaa tgaaagtcac cctagtactt     2400
caaattcagc tcctgcactg gatgctgcag acacgggggca cacaagtact gtacaacctg    2460
aagacatgat tgaaacacgg tatgtccaaa catcacaaac tagggatgag atgagtcttg    2520
agagtttctt agggaggtct ggctgtatac atatatcaca tctaaatgtt aagtatacag     2580
attacaatga aaagaataac tttagatcat ggccaataag tataaaggag atggcacaaa     2640
taagaagaaa gtttgaactt ttcacgtatg tgagatttga ttcagaaatt accctagtgc    2700
```

```
cttgtatagc ctctcaaagt aatgacattg ggcatgtagt gatgcaatac atgtatgtcc      2760
cacctggtgc acccaaacca gaaaagagag atgattacac ttggcaatct ggaactaatg      2820 cttcaattt  ctggcaacac ggtcaacctt accctcgctt tcacttcct ttcttaagca      2880 tagcctcagc ttattacatg ttttatgatg gttatgatgg tgatgttccc gggtcaagat      2940
atgggaccat agtaacaaat gatatgggca cactgtgttc tagaattgta actgaagaac      3000
accaaactca agtcaatatc accacaagga tatatcataa agccaaacat gtgaaagcgt      3060
ggtgcccacg accccaaga gctgtgggtt acacacacac acatgttacc aactacaaac      3120
catcagaagg agactacagt gtcagtattc caattagaga tagccctaga catattctca      3180
atgtgggacc tagtgacatg tatgtacatg tcggcaattt aatatacaga aatttacatc      3240
tttttaattc tgatgtccat gattctatct tagtctctta ttcatctgat ctagtcattt      3300
accgcacaaa cactacaggt gatgactata tcccaacatg tgattgcaca gatgcaactt      3360
attactgtag gcataagaat agatattacc caataaaagt tactagccat gattggtatg      3420
aaatacaaga aagtgagtat tatcccaaac acatccaata taatctctta attggtgaag      3480
gcccatgtga accaggggat tgtggtggaa aactcctttg caagcatggt gtgattggaa      3540
ttattacagc aggtggtgag ggacatgtgg ctttcataga tttgagacat ttccattgtg      3600
cagaagaaca aggtatcaca gactacatac atatgctagg ggaagccttt ggaagtggat      3660
ttgtggacag tgttaaggat caaatcaatg caataaaccc cataataat attagcaaga      3720 aactagttaa atggatcctt aggataatat ctgctatggt gataatcata aggaatagct      3780
cagatccgca aacagttata gctacactta cactaatagg ttgttcagga tcaccatggc      3840
ggtttctaaa ggaaaagttc tgtaaatgga cacagctgca ttatgtacac aaagagtcag      3900
actcatggct taagaaattc acagaaatgt gcaatgcagc aagaggtctt gagtggattg      3960
gaaataaaat atccaaattc atagaatgga tgaagtctat gttgccccag gcccaattaa      4020
aggtcaagta tctcaatgaa cttaaaaagc tgagtttgct ggagaagcag attgagaact      4080
tgcgctgtgc agatgcaaaa acccaggaga aaataaaagt agaagttgat accctccatg      4140
atttatcatg caagttcctt cctttgtatg ctagtgaagc taagagaatc aaagttttgt      4200
acaataaatg caataatata atcaagcaga aaaagaggag tgaaccagtt gctgtgatga      4260
tacatggtcc acctggaact ggtaagtcta taactacaag ctttcttgct aggatgataa      4320
caaatgaaag tgacatttat tcattaccac cagatcccaa atactttgat ggatatgacc      4380
aacagagtgt agttatcatg gatgatataa tgcagaatcc agatgggagag acatgtccc       4440 tgttttgtca gatggtgtca agtgtcacgt ttattccacc aatggccgat ttgccagata      4500
agggtaaacc atttgattct cgttttgtct tctgtagcac aaaccaatcc cttttagctc      4560
caccaactat tacttcactt tctgctatga atagaagatt ttatttagat ttggatataa      4620
ttgtgcatga aaattacaaa aacgcccaag ggaaattgga cgtgtccaga tcttttaaac      4680
catgtgatgt ggatactaaa ataggcaatg caaaatgctg cccattcata tgtggtaagg      4740
ctgtgtcttt taagaccga aacacatgtg aggtatattc tctctgccag atttacaaca      4800
tgattatgca ggaggatagg caccgtagga gtgttgtgga tgtgatgaca gcaatatttc      4860
aaggacctat cacaatgaat gccccaccac cacctgcgat agcagattta ctacaatcag      4920
tcagaactcc agaggtaatt aagtattgtg aagagaacaa gtggataatt ccagcagatt      4980
gtaaaattga gagggattta aatttagcaa acaatattat aacaatcata gcaaatgtta      5040
ttagtatagc tggtattatt tttgttattt acaagttatt ttgtacactc cagggcccat      5100
```

-continued

```
actctgggga gcctaaaccc aaacccaaaa ttccagaaag aagagttgtg gctcaaggac      5160
ctgaagagga atttggtcgc tccctaatta aacataatac atgtgttgtt accacggaga      5220
atggaaaatt cacaggctta ggtatatatg acaaaaccat gattatacca acacatgctg      5280
atccaggtaa gacaatccaa atagatggga taaatgttaa aatttcagac tcttatgatc      5340
tatataataa gaatggtgtg aagcttgaga taacagtggt taaattagat aggaatgaaa      5400
aatttaggga tattcgaaaa tacatcccag agaaggaaga tgattatcca gaatgtaatt      5460
tggccttagt agctaaccag cctgagccta caatactaaa tgtaggtgat gttgtatcat      5520
atggaaatat attacttagt ggaaatcaaa ctgcaagaat gcttaaatac aattatccaa      5580
ctaaatcagg atattgtggg ggggttctgt ataaatagg taatgttctg ggtatacatg       5640
ttggaggtaa tggtaaggat ggattctcag ctacattact cagatcttac tttagtgaga      5700
ctcaaggaca gataacaaaa actgcaaatg ttaaggaaca tggattccct actatacaca      5760
cccctagcaa aaccaaatta caacccagtg tattttatga tgtattcaaa gggaccaaag      5820
aaccagctgt actatctgag aaagatccac gcttagaaac agatttcaag aaagccttat      5880
tttccaaata caaggggaat ctaaactgtg aaataaatga ccatgttaag attgcagttg      5940
cacactattc tgcccaacta atgacacttg atatagattc aaacaatatg agtttagaag      6000
atagtgtgtt tggctcagat ggactagagg ctttggattt gaatactagt gcaggttttc      6060
catacataag catgggaata aagaaaagag acctaatcga caaaaacacc aaagacatat      6120
ctaaacttaa aattgcatta gataaatatg gagtggattt acccatggtc actttccta      6180 aagatgagct tagaaagaaa gagaagatat catctggaaa aactcgtgtc atagaggcta      6240
gcagtgtgaa tgatacagta gcatttagaa tggtatatgg taatttattt gcagcttttc      6300
ataaaaaccc tgggatagta acaggctctg cagttggatg tgatccggaa acattctggt      6360
caaagatccc tgtcatgtta gatggtgaat gcataatggc ttttgattat acaaactacg      6420
atggtagtat acacccaatg tggtttgaag ctttgaaaat ggtattaagt aacttgcaat      6480
ttgaacccag gttaattgat agattgtgta attctaagca tatatacaaa gattcatact      6540
atgaggttga ggggggggtg ccttcaggat gttctggaac aagcatattt aatactatga      6600
tcaataatgt aattataaga acattagtgt tagatgcata caaacatata gatttggata      6660
aattgaaaat aatagcatat ggtgatgatg tgattttctc atacaaatac actcttgata      6720
tggaagcgat tgctcaagag ggcagcaaat atggactaac catcacacct gctgacaaat      6780
ctgagacttt taagaagctt gattatagta atgttacctt tctgaaaaga ggcttcaaac      6840
aagatgaaag atacccattt ttaatccatc caacctttcc aattgatgag atacatgagt      6900
caattagatg gacaaagaaa ccctcacaaa tgcatgagca cattctctca ttgtgtcatt      6960
taatgtggca caatggtcat gaagtctata gagactttga gcggaagata cgcagtgtta      7020
gcgctggacg tgcactgtat atccctcct atgaagtgct cttgcatgag tggtatgaaa       7080
aattttaata gaatatagaa atgataaaca tttagtttat tagttttat                 7129
```

<210> SEQ ID NO 7
<211> LENGTH: 27
<212> TYPE: DNA
<213> ORGANISM: Enterovirus

<400> SEQUENCE: 7
gccggaggac tcactggtag cacacgc        27

```
<210> SEQ ID NO 8
<211> LENGTH: 27
<212> TYPE: DNA
<213> ORGANISM: Enterovirus

<400> SEQUENCE: 8
gccggaggac tcattggtag cacacgg                                          27

<210> SEQ ID NO 9
<211> LENGTH: 28
<212> TYPE: DNA
<213> ORGANISM: enterovirus

<400> SEQUENCE: 9
gccggaggaa atcacaatta gcacacgg                                         28

<210> SEQ ID NO 10
<211> LENGTH: 27
<212> TYPE: DNA
<213> ORGANISM: Enterovirus

<400> SEQUENCE: 10
gccggaggaa tcacaattag cacacgg                                          27

<210> SEQ ID NO 11
<211> LENGTH: 28
<212> TYPE: DNA
<213> ORGANISM: Enterovirus

<400> SEQUENCE: 11
gccggaggaa tcaacaatta gcacacgg                                         28

<210> SEQ ID NO 12
<211> LENGTH: 27
<212> TYPE: DNA
<213> ORGANISM: Enterovirus

<400> SEQUENCE: 12
gccggaggac tcacaattag caaacgc                                          27

<210> SEQ ID NO 13
<211> LENGTH: 27
<212> TYPE: DNA
<213> ORGANISM: Enterovirus

<400> SEQUENCE: 13
gccggaggac tcaaaacaag cacacgg                                          27

<210> SEQ ID NO 14
<211> LENGTH: 27
<212> TYPE: DNA
<213> ORGANISM: Enterovirus

<400> SEQUENCE: 14
gccggaggaa tcaaaacaag cacacgg                                          27

<210> SEQ ID NO 15
<211> LENGTH: 27
<212> TYPE: DNA
<213> ORGANISM: Enterovirus

<400> SEQUENCE: 15
gccggaggac tcaaagcaag cacacgg                                          27
```

<210> SEQ ID NO 16
<211> LENGTH: 27
<212> TYPE: DNA
<213> ORGANISM: Enterovirus

<400> SEQUENCE: 16
gccggaggac tcacacatag cacacgg                                         27

<210> SEQ ID NO 17
<211> LENGTH: 27
<212> TYPE: DNA
<213> ORGANISM: Enterovirus

<400> SEQUENCE: 17
gccggaggaa tcaagatgag cacacgg                                         27

<210> SEQ ID NO 18
<211> LENGTH: 27
<212> TYPE: DNA
<213> ORGANISM: Enterovirus

<400> SEQUENCE: 18
gccggaggag tcaagatgag cacacgg                                         27

<210> SEQ ID NO 19
<211> LENGTH: 27
<212> TYPE: DNA
<213> ORGANISM: Enterovirus

<400> SEQUENCE: 19
gccggaggac tcaagatgag cacacgg                                         27

<210> SEQ ID NO 20
<211> LENGTH: 27
<212> TYPE: DNA
<213> ORGANISM: Enterovirus

<400> SEQUENCE: 20
gccggaggac tcaatgtgag cacacgg                                         27

<210> SEQ ID NO 21
<211> LENGTH: 27
<212> TYPE: DNA
<213> ORGANISM: Enterovirus

<400> SEQUENCE: 21
gccggaggac tcaaggtgag cacacgg                                         27

<210> SEQ ID NO 22
<211> LENGTH: 27
<212> TYPE: DNA
<213> ORGANISM: Enterovirus

<400> SEQUENCE: 22
gccggaggac tcaaagtgag cacacgg                                         27

<210> SEQ ID NO 23
<211> LENGTH: 29
<212> TYPE: DNA
<213> ORGANISM: Enterovirus

<400> SEQUENCE: 23
gccggaggac atcaaagtga gcagcacgg                                    29

<210> SEQ ID NO 24
<211> LENGTH: 27
<212> TYPE: DNA
<213> ORGANISM: Enterovirus

<400> SEQUENCE: 24
gccggaggac tcaaagcgag cacacgg                                      27

<210> SEQ ID NO 25
<211> LENGTH: 27
<212> TYPE: DNA
<213> ORGANISM: Enterovirus

<400> SEQUENCE: 25
gccggaggac tcaaagtgag cacacgc                                      27

<210> SEQ ID NO 26
<211> LENGTH: 27
<212> TYPE: DNA
<213> ORGANISM: Enterovirus

<400> SEQUENCE: 26
gccggaggac tcaaaatgag cacactg                                      27

<210> SEQ ID NO 27
<211> LENGTH: 27
<212> TYPE: DNA
<213> ORGANISM: Enterovirus

<400> SEQUENCE: 27
gccggaggac tcaaagtgag cacaata                                      27

<210> SEQ ID NO 28
<211> LENGTH: 28
<212> TYPE: DNA
<213> ORGANISM: Enterovirus

<400> SEQUENCE: 28
gccggaggac tcaaaagtga gcacaata                                     28

<210> SEQ ID NO 29
<211> LENGTH: 27
<212> TYPE: DNA
<213> ORGANISM: Enterovirus

<400> SEQUENCE: 29
gccggaggaa tcaaggtgag cacaata                                      27

<210> SEQ ID NO 30
<211> LENGTH: 27
<212> TYPE: DNA
<213> ORGANISM: Enterovirus

<400> SEQUENCE: 30
gccggaggac tcaaggtgag cacagta                                      27

<210> SEQ ID NO 31
<211> LENGTH: 27
<212> TYPE: DNA
<213> ORGANISM: Enterovirus

<400> SEQUENCE: 31
gccggaggac tcaaagtgag cacagta                                              27

<210> SEQ ID NO 32
<211> LENGTH: 27
<212> TYPE: DNA
<213> ORGANISM: Enterovirus

<400> SEQUENCE: 32
gccggaggac taccaattag ctcaata                                              27

<210> SEQ ID NO 33
<211> LENGTH: 27
<212> TYPE: DNA
<213> ORGANISM: Enterovirus

<400> SEQUENCE: 33
gccggaggac tccaagtgag cgcagta                                              27

<210> SEQ ID NO 34
<211> LENGTH: 27
<212> TYPE: DNA
<213> ORGANISM: Enterovirus

<400> SEQUENCE: 34
gccggaggac tcaaagtgag cacacta                                              27

<210> SEQ ID NO 35
<211> LENGTH: 27
<212> TYPE: DNA
<213> ORGANISM: Enterovirus

<400> SEQUENCE: 35
gccggaggac tcacatgaag cacactc                                              27

<210> SEQ ID NO 36
<211> LENGTH: 67
<212> TYPE: DNA
<213> ORGANISM: Enterovirus

<400> SEQUENCE: 36
ykgacatggt gtgaagagtc tattgagctc masttgrkag tcctccggcc cctgaatgcg          60
gctatcc                                                                    67

<210> SEQ ID NO 37
<211> LENGTH: 27
<212> TYPE: DNA
<213> ORGANISM: Enterovirus

<400> SEQUENCE: 37
gccggaggac tcaaggtgag cacacgc                                              27

<210> SEQ ID NO 38
<211> LENGTH: 27
<212> TYPE: DNA
<213> ORGANISM: Enterovirus

<400> SEQUENCE: 38
gccggaggac tcattggtag cacacgg                                              27